(12) United States Patent
Xu et al.

(10) Patent No.: US 11,639,725 B2
(45) Date of Patent: May 2, 2023

(54) MICRO WATER PUMP

(71) Applicant: AAC Microtech (Changzhou) Co., Ltd., Changzhou (CN)

(72) Inventors: Detao Xu, Shenzhen (CN); Sensen Yang, Shenzhen (CN)

(73) Assignee: AAC Microtech (Changzhou) Co., Ltd., Changzhou (CN)

( * ) Notice: Subject to any disclaimer, the term of this patent is extended or adjusted under 35 U.S.C. 154(b) by 0 days.

(21) Appl. No.: 17/534,387

(22) Filed: Nov. 23, 2021

(65) Prior Publication Data
US 2022/0170479 A1 Jun. 2, 2022

(30) Foreign Application Priority Data

Nov. 27, 2020 (CN) .......................... 202022813102.9

(51) Int. Cl.
| | |
|---|---|
| *F04D 29/42* | (2006.01) |
| *F04D 13/06* | (2006.01) |
| *F04D 29/62* | (2006.01) |
| *F04D 1/00* | (2006.01) |
| *F04D 29/22* | (2006.01) |
| *F04D 29/041* | (2006.01) |

(Continued)

(52) U.S. Cl.
CPC ......... *F04D 29/426* (2013.01); *A61M 60/148* (2021.01); *A61M 60/232* (2021.01); *A61M 60/419* (2021.01); *A61M 60/422* (2021.01); *A61M 60/81* (2021.01); *F04D 1/00* (2013.01); *F04D 13/06* (2013.01); *F04D 13/0606* (2013.01); *F04D 13/0666* (2013.01); *F04D 29/041* (2013.01); *F04D 29/043* (2013.01); *F04D 29/047* (2013.01); *F04D 29/048* (2013.01); *F04D 29/0413* (2013.01); *F04D 29/0473* (2013.01); *F04D 29/22* (2013.01); *F04D 29/628* (2013.01)

(58) Field of Classification Search
CPC .. F04D 29/048; F04D 13/0666; F04D 29/047; F04D 13/06; F04D 29/426; F04D 29/628; F04D 29/22; F04D 29/043; F04D 29/0413; F04D 1/00; F04D 29/0473; F04D 13/0673; F04D 29/041; F04D 13/0606; A61M 60/422; A61M 60/148; A61M 60/824; A61M 60/232; A61M 60/419; A61M 60/81
See application file for complete search history.

(56) References Cited

U.S. PATENT DOCUMENTS

| | | | |
|---|---|---|---|
| 7,016,195 B2* | 3/2006 | Ito | G06F 1/203 |
| | | | 174/15.1 |
| 10,724,544 B2* | 7/2020 | Graham | F04D 29/284 |
| 2006/0171801 A1* | 8/2006 | Manabe | H01L 23/473 |
| | | | 415/176 |

* cited by examiner

*Primary Examiner* — Peter J Bertheaud
(74) *Attorney, Agent, or Firm* — W&G Law Group (57) ABSTRACT

The present disclosure provides a micro water pump, including: a pump body having a cavity, an inlet communicating with the cavity, and an outlet communicating with the cavity; a drive mechanism installed on the pump body for driving liquid from the inlet into the cavity and discharging from the outlet. The pump body includes a base, an upper cover engaging with the base for forming the cavity, and a barrier member. The upper cover includes a fixed wall located in the cavity. The barrier member protrudes from the fixed wall for preventing the drive mechanism from colliding and rubbing with the fixed wall during rotation. By virtue of the configuration, improved heat-dissipation performance is performed.

7 Claims, 8 Drawing Sheets

(51) Int. Cl.
*F04D 29/048* (2006.01)
*F04D 29/043* (2006.01)
*F04D 29/047* (2006.01)
*A61M 60/148* (2021.01)
*A61M 60/81* (2021.01)
*A61M 60/232* (2021.01)
*A61M 60/422* (2021.01)
*A61M 60/419* (2021.01)

MICRO WATER PUMP

FIELD OF THE PRESENT DISCLOSURE

The present disclosure relates to fluid machinery, in particular to a micro water pump.

DESCRIPTION OF RELATED ART

The heating element of the electronic device generates a large amount of heat during the work project. If the heat is not discharged in time, the internal temperature of the electronic device will rise sharply, thereby affecting the working efficiency of the electronic components in the electronic device. Liquid cooling is a better cooling method. The heat emitted by the heating element is absorbed by connecting the heating element with the cooling pipeline. Use the coolant flow in the pipeline to drain the heat-absorbing high-temperature coolant and replenish the low-temperature coolant. In order to speed up the flow of the cooling liquid, a micro water pump is generally connected to the pipeline, and the flow speed of the cooling liquid is accelerated by the micro water pump.

The related technology micro water pump comprises the upper cover and the lower cover which are assembled together, and the impeller and magnetic parts installed on the lower cover. The upper cover and the lower cover enclose a accommodating space. The magnetic member drives the impeller to rotate in the receiving space. The impeller rotates under the force of the magnetic field generated by the magnetic member, and the micro impeller drives the cooling liquid to circulate. However, during the working process of the micro water pump, the impeller will float up and down and collide and rub against the upper cover. As a result, noise is generated, the rotation resistance of the impeller is increased, and the driving efficiency of the micro water pump is reduced.

Therefore, it is necessary to study a new type of micro water pump to solve the above problems.

SUMMARY OF THE PRESENT INVENTION

One of the objects of the present invention is to provide a micro water pump with improved heat-dissipation performance.

To achieve the above-mentioned objects, the present invention provides a micro water pump, comprising: a pump body having a cavity, an inlet communicating with the cavity, and an outlet communicating with the cavity; a drive mechanism installed on the pump body for driving liquid from the inlet into the cavity and discharging from the outlet. Wherein the pump body comprises a base, an upper cover engaging with the base for forming the cavity, and a barrier member. The upper cover comprises a fixed wall located in the cavity. The barrier member protrudes from the fixed wall for preventing the drive mechanism from colliding and rubbing with the fixed wall during rotation.

In addition, the micro water pump further includes a rotating shaft formed by the base, wherein the drive mechanism comprises an impeller located in the cavity for being rotatably connected with the rotating shaft, a rotor engaged with the impeller, and a stator mounted on the base for driving the rotor to rotate; and, the impeller is opposite to the barrier member.

In addition, the fixed wall defines a fixing slot; the barrier member is located in the fixing slot and protrudes from a surface of the fixed wall along the rotation axis of the impeller; a projection of the barrier member overlaps a projection of the impeller.

In addition, the barrier member is in the shape of a thin ring sheet, which is made of polyimide.

In addition, the barrier member is in the shape of a thin ring sheet, which is made of polyimide.

In addition, the barrier member is in the shape of a thin ring sheet, which is made of polyimide.

In addition, the impeller comprises an impeller body, a first installation slot arranged at one end of the impeller body, and a blade arranged on an outer sidewall of the impeller body; the blade body is rotatably connected with the rotating shaft; the rotor is a circular magnet installed in the first installation slot.

In addition, the rotor is fixed to the inner sidewall of the first installation slot or the outer sidewall of the impeller body by gluing.

In addition, a second installation slot is provided on the side of the base opposite to the upper cover; the stator is embedded in the second installation slot.

In addition, the micro water pump further comprises a circuit board installed on the base; wherein a side of the base back to the upper cover is provided with a third installation slot for embedding the circuit board; the circuit board is electrically connected to the state via a cable.

In addition, the micro water pump further comprises a sealing ring; wherein one of the base and the upper cover includes a sealed groove surrounding the cavity for accommodating the sealing ring and being squeezed by the base and the upper cover for sealing the cavity.

BRIEF DESCRIPTION OF THE DRAWINGS

Many aspects of the exemplary embodiments can be better understood with reference to the following drawings. The components in the drawing are not necessarily drawn to scale, the emphasis instead being placed upon clearly illustrating the principles of the present disclosure.

DETAILED DESCRIPTION OF THE EXEMPLARY EMBODIMENTS

The present disclosure will hereinafter be described in detail with reference to exemplary embodiments. To make the technical problems to be solved, technical solutions and beneficial effects of the present disclosure more apparent, the present disclosure is described in further detail together with the figures and the embodiments. It should be understood the specific embodiments described hereby is only to explain the disclosure, not intended to limit the disclosure.

It should be noted that all directional indicators (such as up, down, left, right, front, back, inside, outside, top, bottom . . . ) in the embodiments of the present invention are only used to explain that they are in a specific posture (As shown in the Fig. below), the relative positional relationship between the components, etc., if the specific posture changes, the directional indication will also change accordingly.

It should also be noted that when an element is referred to as being "fixed on" or "arranged on" another element, the element may be directly on the other element or there may be a centering element at the same time. When an element is referred to as being "connected" to another element, it can be directly connected to the other element or an intermediate element may be present at the same time.

As shown in FIGS. 1-8, an embodiment of the present invention proposes a micro water pump 100, which comprises a pump body 10 and a drive mechanism 20. The pump body 10 is provided with a cavity 18, an inlet 116 connected to the cavity 18, and an outlet 117 connected to the cavity 18. The drive mechanism 20 is installed on the pump body 10 to drive liquid from the inlet 116 into the cavity 18 and discharged from the outlet 117.

Wherein, the pump body 10 comprises a base 11, an upper cover 12 assembled with the base 11, a barrier member 13 installed on the upper cover 12, a rotating shaft 14 installed on the base 11, and a sealing ring 15 sandwiched between the base 11 and the upper cover 12, a circuit board 16 fixed on the outer wall of the base 11, and a screw 17 fixing the base 11 and the upper cover 12 together. The base 11 and the upper cover 12 are assembled to form the cavity 18. The sealing ring 15 surrounds the cavity 18 and is clamped and squeezed between the base 11 and the upper cover 12 to seal the cavity 18. The drive mechanism 20 is electrically connected to the circuit board 16 to control the operation of the drive mechanism 20. The upper cover 12 comprises a fixed wall 1221 located in the cavity 18. The barrier member 13 is protruded from the fixed wall 1221 to prevent the drive mechanism 20 from colliding and rubbing with the fixed wall 1221 during rotation. Optionally, the barrier member 13 is in the shape of a ring sheet, which is made of polyimide.

Figure 1:
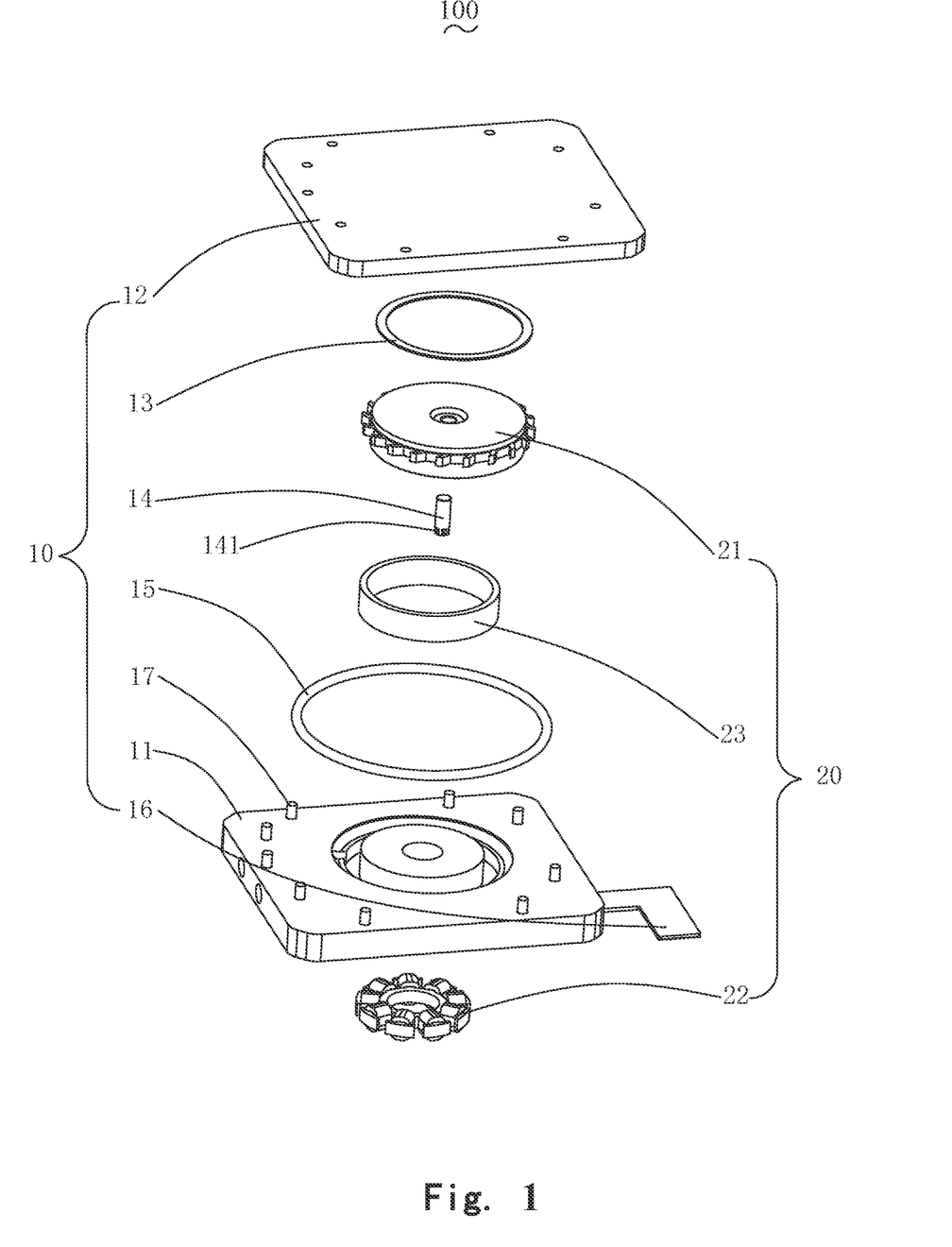
FIG. 1 is an isometric and exploded view of a micro water pump in accordance with an exemplary embodiment of the present disclosure.
Figure 2:
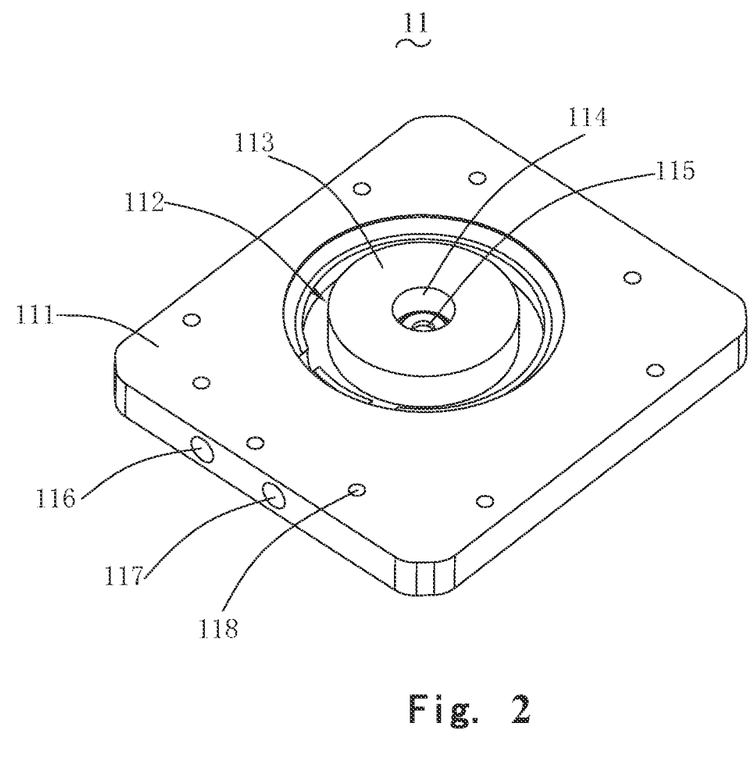
FIG. 2 is an isometric view of a base of the micro water pump shown in FIG. 1.
Figure 3:
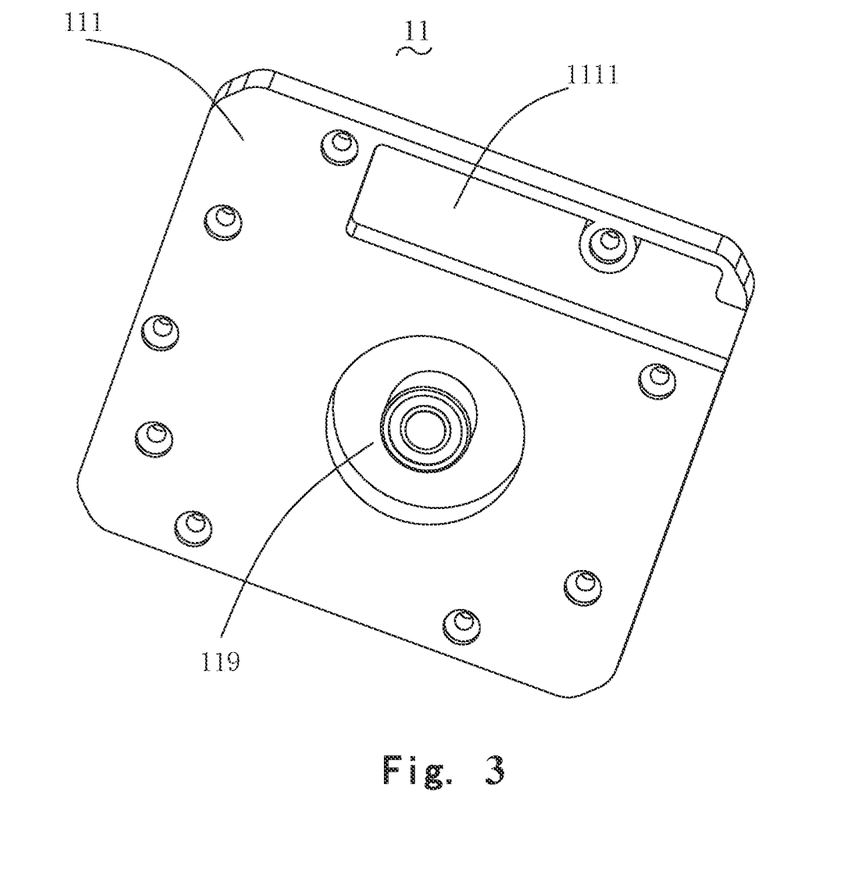
FIG. 3 is an isometric view of the base in FIG. 2, from another aspect.

Specifically, as shown in FIGS. 1-3, the base 11 comprises a square base body 111, a first concave part 112 arranged on the opposite side of the base body 111 and the upper cover 12, and a protruding platform 113 protruding from the first concave part 112, a first concave hole 114 provided on the protruding platform 113, a second concave hole 115 provided on the inner bottom wall of the first concave hole 114, and the plurality of holes penetrating the base body 11, and a second installation slot 119 and a third installation slot 1111 located on the side of the base body 111 away from the upper cover 12. Wherein, the first concave part 112 and the second installation slot 119 both are in a ring shape. The inner diameter of the first concave part 112 is larger than the outer diameter of the second installation slot 119. In order to surround the second installation slot 119 in it. The inlet 116 and the outlet 117 are connected to the first concave part 112 respectively. The third installation slot 1111 is a long strip structure, and the circuit board 16 is installed in the third installation slot 1111.

The rotating shaft 14 is roughly cylindrical, one end of which is fixed in the second concave hole 115 of the base 11. Specifically, the rotating shaft 14 is fixed in the second concave hole 115 by glue bonding. In order to increase the firmness of the bonding between the rotating shaft 14 and the base 11, a plurality of pits 141 are provided on the outer periphery of the rotating shaft 14. The pit 141 can further attach and hold the amount of glue to the rotating shaft 14, so as to enhance the firmness of the rotating shaft 14 on the base 11 when the glue is solidified. In other embodiments, the rotating shaft 14 may be formed on the base 11 by over-injection.

Figure 4:
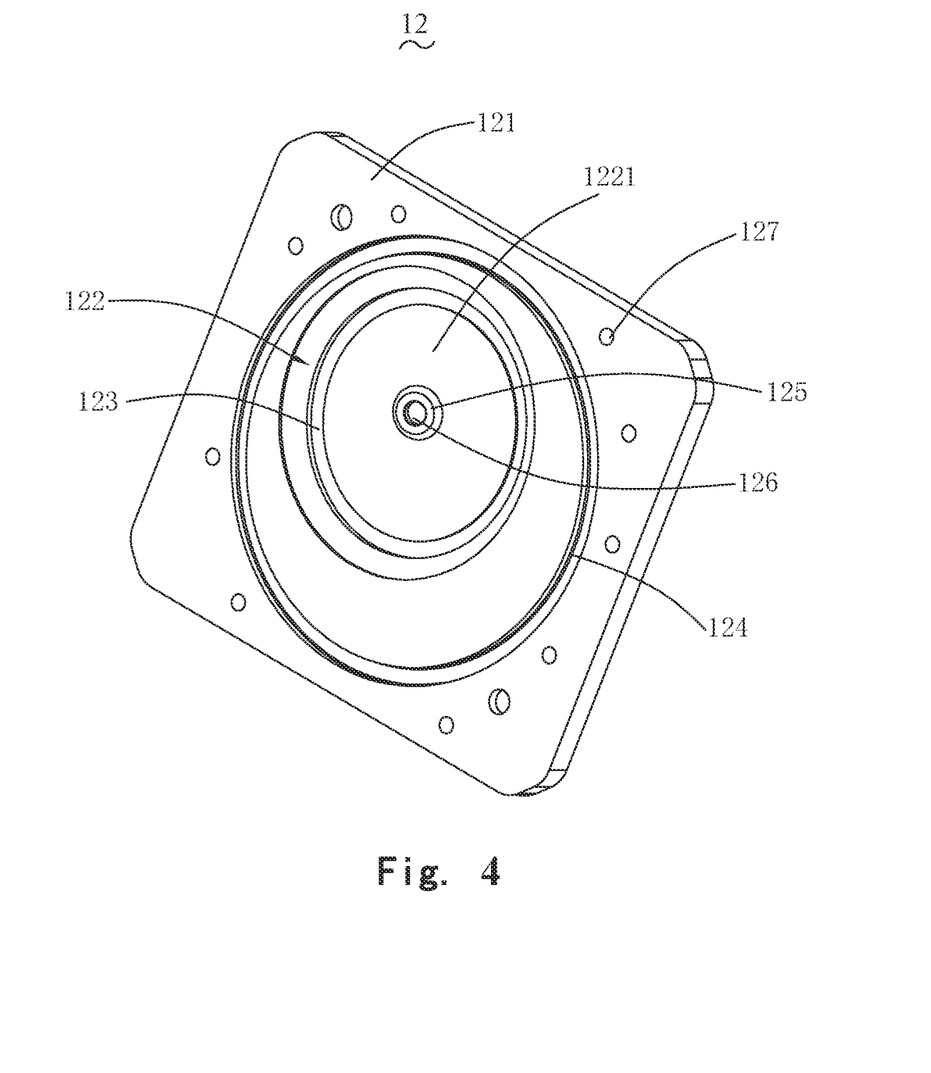
FIG. 4 is an isometric view of a cover of the micro water pump shown in FIG. 1.

The upper cover 12 comprises a cover 121, a second concave part 122 arranged on the side of the cover 121 close to the base 11 and having a fixed wall 1221, a fixing slot 123 arranged on the fixed wall 1221, a sealed groove 124 surrounding the second concave part 122, a convex post 125 provided on the fixed wall 1221, a third concave hole 126 provided on the convex post 125, and a plurality of second fixing holes 127 passing through the cover 121. Wherein, the second concave part 122 and the first concave part 112 are arranged correspondingly. The fixed wall 1221 is arranged opposite to the protruding platform 113. The fixing slot 123 is a ring shape. The barrier member 13 is installed on the fixing slot 123 and protrudes from the surface of the fixed wall 1221.

In other embodiments, the sealed groove 124 may also be provided on the base 11, or the base 11 and the upper cover 12 are provided with the sealed groove 124 at corresponding positions.

Please refer to FIGS. 1-8 together. When the pump body 10 is assembled, the base 11 and the upper cover 12 are assembled together. The end of the rotating shaft 14 away from the base 11 is installed in the third concave hole 126 of the upper cover 12. The screw 17 is screwed into the first fixing hole 118 and the second fixing hole 127 to tightly fit and attach the base body 111 and the cover 121 together. The first concave part 112 and the second concave part 122 are closed and connected to form the cavity 118. The sealing ring 15 is installed on the sealed groove 124 and squeezed by the base body 111 and the cover 121 to seal the cavity 18.

Further, the drive mechanism 20 comprises an impeller 21 arranged in the cavity 18, a stator 22 fixed in the second installation slot 119 of the base 11, and a rotor 23 fixedly connected to the impeller 21.

Figure 5:
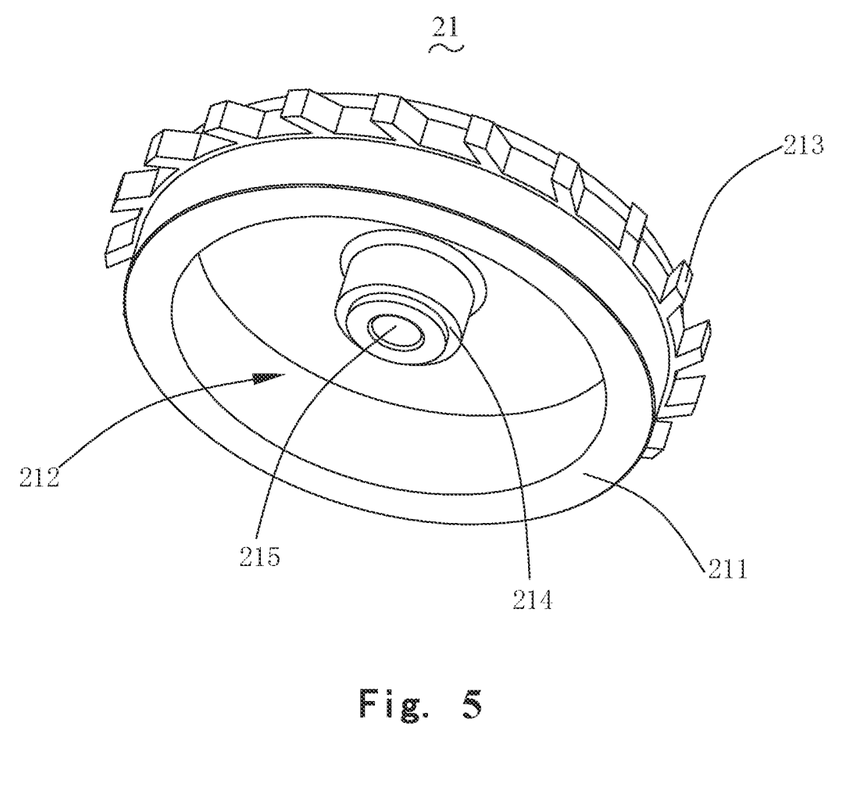
FIG. 5 is an isometric view of an impeller of the micro water pump shown in FIG. 1.
Figure 6:
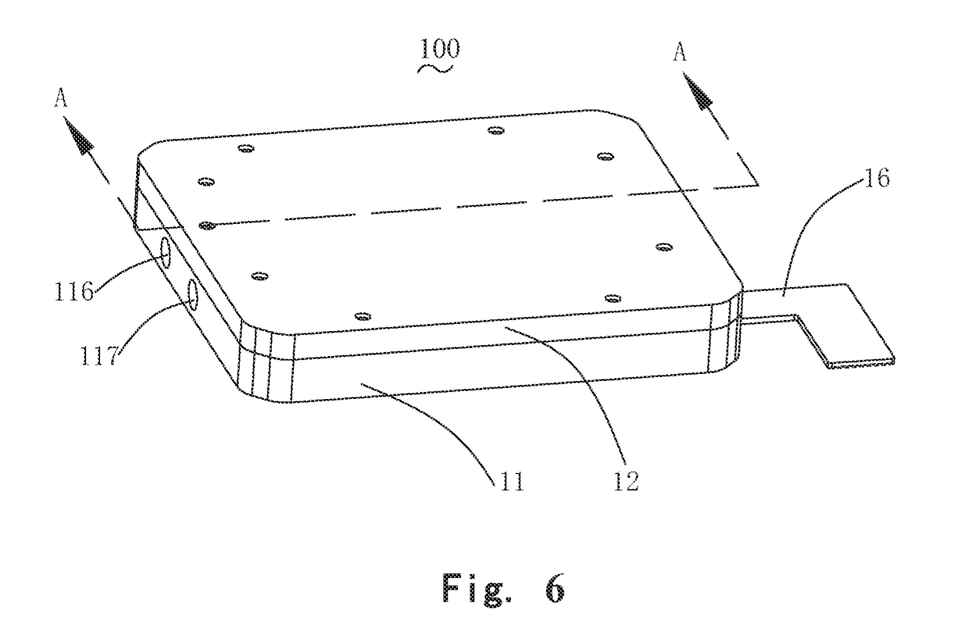
FIG. 6 is an isometric and assembled view of the micro water pump.
Figure 7:
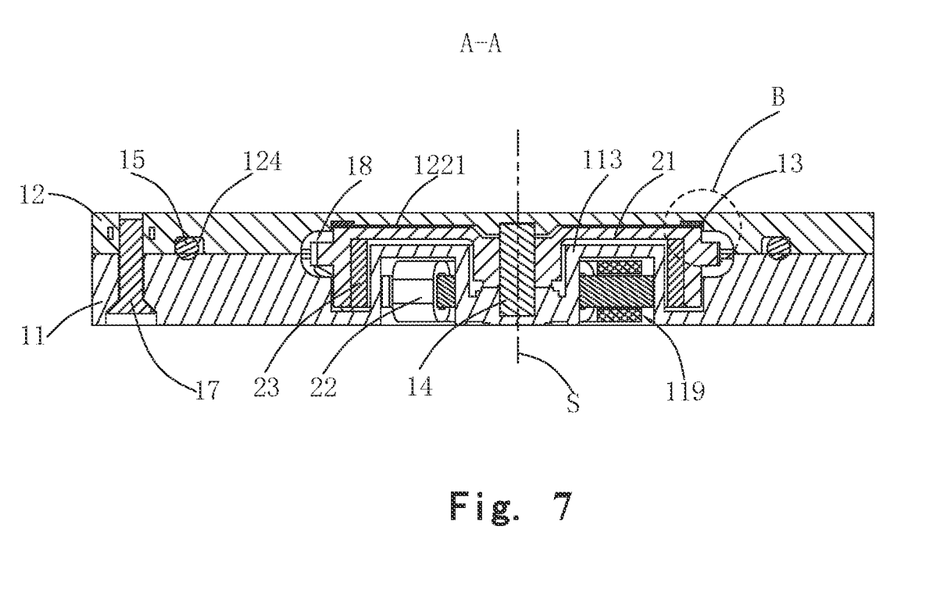
FIG. 7 is cross-sectional view of the micro water pump taken along line AA in FIG. 6.
Figure 8:
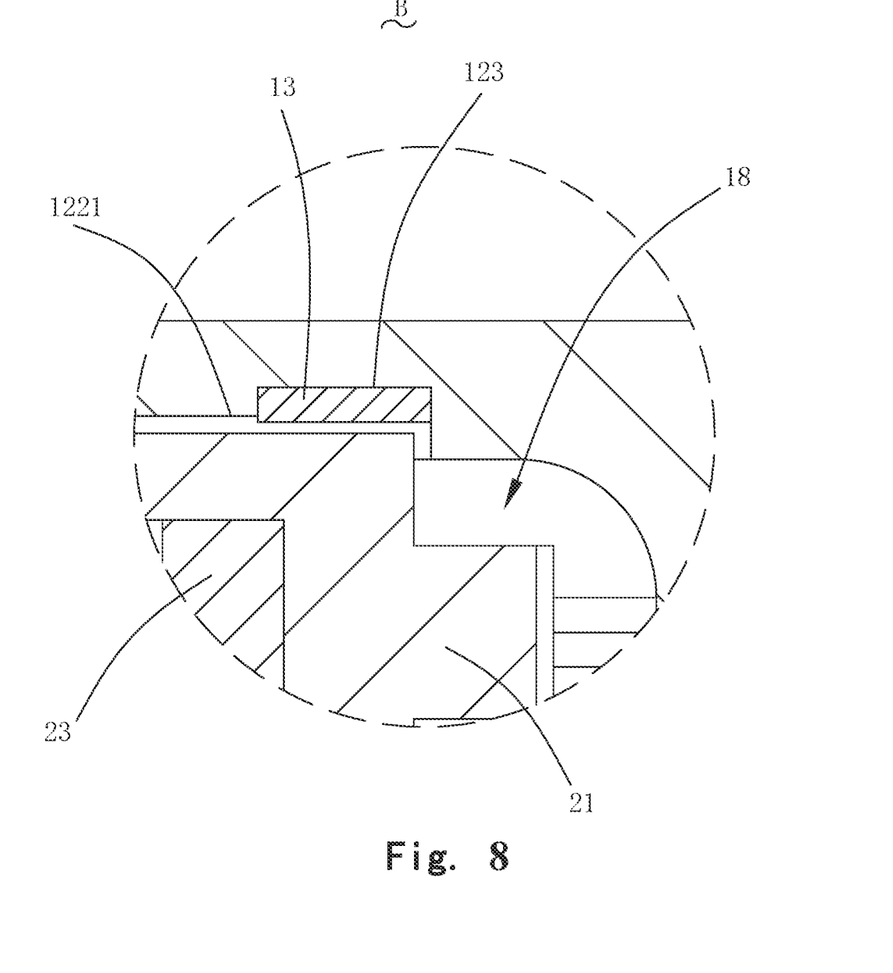
FIG. 8 is an enlarged view of circled Part B in FIG. 7.

Specifically, the impeller 21 comprises an impeller body 211 in cylindrical shape, a first installation slot 212 in cylindrical shape arranged at one end of the impeller body 211, a blade 213 arranged on the outer sidewall of the impeller body 211, and a rotating part 214 protruding from the inner bottom wall of the first installation slot 212 and a shaft hole 215 that penetrates the rotating part 214 and the impeller body 211. The rotor 23 is in a ring shape and is fixed to the inner sidewall of the first installation slot 212 or the outer sidewall of the impeller body 211 by gluing. The impeller body 211 and the rotor 23 are wrapped and the protruding platform 113 of the base 11 is accommodated therein. The rotating part 214 is accommodated in the first concave hole 114. The shaft hole 215 is sleeved on the rotating shaft 14 so that the blade body 211 and the rotating shaft 14 are rotatably connected. Optionally, the rotor 22 is a circular magnet.

In other embodiments, the rotor 23 can be fixed to the outer sidewall of the impeller body 211 by gluing.

The stator 22 is used to drive the rotor 23 to rotate, and the circuit board 16 is electrically connected by a cable, for controlling the rotation of the rotor 23 via the stator. The impeller body 211 of the impeller 21 is spaced from the barrier member 13. Along the rotation axis S of the impeller 21, the projections of the barrier member 13 and the impeller body 211 at least partially overlap.

During the working process of the micro water pump 100, the circuit board 16 passes a variable frequency current to the stator 22. According to the principle of electromagnetic induction, the stator 22 generates a rotating magnetic field, and the rotor 23 rotates under the action of ampere force in the rotating magnetic field. The rotating rotor 23 drives the impeller 21 to rotate.

The liquid enters the cavity 18 from the inlet 116, and is driven by the impeller 21 to rotate at a high speed and perform centrifugal movement. When the liquid reaches the outlet 117, it is thrown out from the outlet 117. After the liquid is thrown out, the pressure in the cavity 18 decreases and is much lower than the atmospheric pressure. The external fluid is replenished into the cavity 18 from the inlet 116 under the action of atmospheric pressure, and the above-mentioned actions are repeatedly realized to realize the liquid transportation.

It is to be understood, however, that even though numerous characteristics and advantages of the present exemplary embodiments have been set forth in the foregoing description, together with details of the structures and functions of the embodiments, the disclosure is illustrative only, and changes may be made in detail, especially in matters of shape, size, and arrangement of parts within the principles of the invention to the full extent indicated by the broad general meaning of the terms where the appended claims are expressed.

What is claimed is:

1. A micro water pump, comprising:
    a pump body having a cavity, an inlet communicating with the cavity, and an outlet communicating with the cavity, comprising a base, an upper cover engaging with the base for forming the cavity, and a barrier member;
    a drive mechanism installed on the pump body for driving liquid from the inlet into the cavity and discharging from the outlet;
    a rotating shaft installed on the base; and
    a circuit board installed on the base; wherein
    the upper cover comprises a fixed wall located in the cavity; the barrier member protrudes from the fixed wall for preventing the drive mechanism from colliding and rubbing with the fixed wall during rotation;
    the drive mechanism comprises an impeller located in the cavity for being rotatably connected with the rotating shaft, a rotor engaged with the impeller, and a stator mounted on the base for driving the rotor to rotate; and, the impeller is opposite to the barrier member;
    the impeller comprises an impeller body, a first installation slot arranged at one end of the impeller body, and a blade arranged on an outer sidewall of the impeller body; the blade body is rotatably connected with the rotating shaft the rotor is a circular magnet installed in the first installation slot;
    a second installation slot is provided on the side of the base opposite to the upper cover; the stator is embedded in the second installation slot;
    a side of the base away from the upper cover is provided with a third installation slot for embedding the circuit board; the circuit board is electrically connected to the stator via a cable.

2. The micro water pump as described in claim 1, wherein the fixed wall defines a fixing slot; the barrier member is located in the fixing slot and protrudes from a surface of the fixed wall along the rotation axis of the impeller; a projection of the barrier member overlaps a projection of the impeller.

3. The micro water pump as described in claim 1, wherein the barrier member is in the shape of a thin ring sheet, which is made of polyimide.

4. The micro water pump as described in claim 1, wherein the barrier member is in the shape of a thin ring sheet, which is made of polyimide.

5. The micro water pump as described in claim 2, wherein the barrier member is in the shape of a thin ring sheet, which is made of polyimide.

6. The micro water pump as described in claim 1, wherein the rotor is fixed to the inner sidewall of the first installation slot or the outer sidewall of the impeller body by gluing.

7. The micro water pump as described in claim 1 further comprising a sealing ring; wherein one of the base and the upper cover includes a sealed groove surrounding the cavity for accommodating the sealing ring and being squeezed by the base and the upper cover for sealing the cavity.

* * * * *